US010384027B2

(12) United States Patent
Harrison

(10) Patent No.: US 10,384,027 B2
(45) Date of Patent: Aug. 20, 2019

(54) NASAL MASK FOR USE IN VARIOUS POSITIVE AIRWAY PRESSURE SUPPLY SYSTEMS

(71) Applicant: Donald Harrison, Park City, UT (US)

(72) Inventor: Donald Harrison, Park City, UT (US)

(73) Assignee: Breas Medical, Inc., North Billerica, MA (US)

( * ) Notice: Subject to any disclaimer, the term of this patent is extended or adjusted under 35 U.S.C. 154(b) by 653 days.

(21) Appl. No.: 14/923,796

(22) Filed: Oct. 27, 2015

(65) Prior Publication Data

US 2016/0228663 A1 Aug. 11, 2016

Related U.S. Application Data

(60) Provisional application No. 62/069,294, filed on Oct. 27, 2014.

(51) Int. Cl.
| | |
|---|---|
| *A61M 16/06* | (2006.01) |
| *A61M 16/10* | (2006.01) |
| *A61M 16/00* | (2006.01) |
| *A61M 16/22* | (2006.01) |
| *A61M 16/08* | (2006.01) |

(52) U.S. Cl.
CPC ........ *A61M 16/06* (2013.01); *A61M 16/0057* (2013.01); *A61M 16/1045* (2013.01); *A61M 16/22* (2013.01); *A61M 16/0616* (2014.02); *A61M 16/0683* (2013.01); *A61M 16/0816* (2013.01); *A61M 2202/0225* (2013.01); *A61M 2210/0618* (2013.01)

(58) Field of Classification Search
CPC .............. A61M 16/06; A61M 16/0605; A61M 16/0611; A61M 16/0616; A61M 16/0622; A61M 16/0633; A61M 16/0638
See application file for complete search history.

(56) References Cited

U.S. PATENT DOCUMENTS

| | | | | |
|---|---|---|---|---|
| 2,470,297 A | * | 5/1949 | Fields ................... | A61M 15/00 128/203.15 |
| 4,907,584 A | * | 3/1990 | McGinnis ............. | A61M 16/06 128/206.24 |
| 5,746,201 A | * | 5/1998 | Kidd ..................... | A61M 16/06 128/205.25 |
| 7,007,696 B2 | * | 3/2006 | Palkon .................. | A61M 16/06 128/206.24 |
| 8,616,209 B2 | * | 12/2013 | Amarasinghe ........ | A61M 16/06 128/205.25 |
| 2003/0019496 A1 | * | 1/2003 | Kopacko ............... | A61M 16/06 128/206.24 |
| 2006/0169286 A1 | * | 8/2006 | Eifler .................... | A61M 16/06 128/206.21 |
| 2010/0006101 A1 | * | 1/2010 | McAuley .............. | A61M 16/06 128/206.24 |
| 2011/0186051 A1 | * | 8/2011 | McAuley .............. | A61M 16/06 128/206.24 |
| 2011/0240030 A1 | * | 10/2011 | Ho ........................ | A61M 16/06 128/206.21 |
| 2012/0090618 A1 | * | 4/2012 | Kwok .................... | A61B 5/097 128/206.24 |

(Continued)

*Primary Examiner* — LaToya M Louis
(74) *Attorney, Agent, or Firm* — Ian Yi Liu

(57) ABSTRACT

A semi-malleable nasal mask system which includes an internal support structure for providing a uniform-like sealing force around the user's nose and nose area.

18 Claims, 8 Drawing Sheets

(56) References Cited

U.S. PATENT DOCUMENTS

2012/0247475 A1* 10/2012 Hernandez ............ A61M 16/06
128/206.24
2013/0098359 A1* 4/2013 Becker .............. A61M 16/0666
128/201.13

* cited by examiner

NASAL MASK FOR USE IN VARIOUS POSITIVE AIRWAY PRESSURE SUPPLY SYSTEMS

PRIORITY CLAIM

Priority is claimed to U.S. Provisional Patent Application Ser. No. 62/069,294 filed Oct. 27, 2014, which is incorporated herein by reference in its entirety.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present invention relates to a positive airway pressure [PAP] devices, such as continuous positive airway pressure [CPAP] devices, and more particularly a method for attenuating the noise released therefrom.

2. Description of the Prior Art

It is known that applying a CPAP device to a patient may prevent upper airway occlusion during sleep. CPAP devices have become the apparatus of choice for the treatment of chronic sleep apnea, chronic pulmonary obstruction and snoring. Many CPAP machines are readily available in the marketplace.

A typical CPAP system generally includes a bedside generator comprising, a blower unit powered by an electric motor. The blower unit, the motor, and associated controls are usually encased together within the bedside generator. A delivery tube, which typically includes a flexible plastic tube having a proximal end and a distal end, is used to deliver pressurized air or other gasses to the patient. The proximal end of the delivery tube is connected to the bedside generator and the distal end of the delivery tube is fitted to the face of a patient, typically via some sort of mask unit that is provided around either the nose or mouth of the patient. The mask unit can include features which allow the mask to be affixed to the patient and maintain a proper orientation with respect to the patient's airways.

It will be appreciated that CPAP machines are typically large and heavy. However, recent developments have provided for smaller and lighter CPAP machines. It will be appreciated that because the apparatus is used during sleep, that the weight of such units should be reduced while the comfort should be increased as much as possible so as to allow the user to more easily sleep while wearing the mask.

SUMMARY OF THE INVENTION

The system and methods described herein provide a CPAP apparatus that includes a nasal mask for interfacing with a user's airways, the nasal mask having a pliable portion having an interior support structure forming a cavity which can be placed over so as to encompass the user's nose. The nasal mask can also be configured to couple to a rigid air supply adapter which can have various features incorporated therein such as carbon dioxide washout vents, heat-moisture exchange units, etc. The air supply adapter can be configured to attach to a positive air pressure supply and direct a supply of positive air pressure into the internal cavity of the nasal mask. In some embodiments an intermediate coupler can be provided between the semi-flexible nasal mask and the rigid air supply adapter.

In yet additional embodiments the nasal mask can be configured to attach to a headgear assembly for providing proper tension and placement on the user's face. A headgear attachment interface can include one or more attachments points or anchors which are structurally coupled to the interior support structure of the nasal mask. In yet additional embodiments the nasal mask can be provided with one or more malleable sealing membranes which are configured to conform to and seal around the nose of the patient, i.e. around the bridge of the nose and below the nose on the maxilla of the patient above the patient's upper lip. When provided in multiples these malleable sealing membranes can be provided in echelon one upon another, and can have varying durometers so as to provide an adequate yet comfortable seal around the patient's nose.

In one embodiment a nasal mask comprises an internal support structure having an external shell disposed or formed over the internal support structure. A plurality of attachment mechanisms can be provided about the external surface of the external shell and mechanically coupled to the internal support structure. Formed in the shell on one end is a user interface aperture that can be formed to be placed over a user's nose or nasal region. Formed on another end of the nasal mask is an inlet aperture that can be coupled to a flowing gas source or pressurized gas source. The attachment mechanisms can allow for straps or a headgear system to be attached thereto and when a force is applied to the attachment mechanisms that force is transferred through to the internal support structure and shell, which can deform the user interface aperture about the user's nose or nasal region and form seal.

In some embodiments the internal support structure transfers the force uniformly. In other embodiments the internal support structure transfers the force and causes deformation about the portions of the user interface aperture that are most likely to leak or be more difficult to seal about the user's nose or nasal region. In some embodiments a y-shaped strapped is used to provide tension in a directed way that allows the mask to conform optimally about a user's nose region.

In some embodiments the nasal mask can be formed of multiple components including a malleable mask portion, a rigid input adaptor that couples to a flowing gas source, and an intermediate coupler that connects the malleable mask portion to the input adaptor. Each of the components can be formed of different materials, have different durometers, or vary in thickness.

In some embodiments, the user can use the same input adaptor and intermediate coupler to adapt to a variety of masks that differ in size, malleability, color, shape, weight and so forth. The masks can be configured to be periodically replaced for hygienic purposes.

Additional features that can be disposed or formed as part of the nasal mask system include: removable HME units disposed towards the front portion of the mask and allow flowing gas to come in, but trap moisture; integrated $CO_2$ vents; removable $CO_2$ vents that vary in dissipation capacity; and straps or headgear systems that secure to the attachment mechanisms and provide a force on the nasal mask.

The user interface aperture can also be provided with one or more malleable membranes that help form a sealing region about the user's nose when a force is applied to the mask. The membranes can be directly attached to the internal support structure or formed as part of the shell disposed over the internal support structure. The membranes in some embodiments can be removable and replaceable. Similar to swapping out mask components the membranes can be configure to detach from the mask and have a variety of thicknesses, shapes, durometers, colors and so forth.

Embodiments with a rigid coupler can be overmolded onto the external shell of the nasal mask and vice versa.

Some attachment mechanisms are formed of a plurality of circular grommets being configured to affix to corresponding loops of a strap or headgear assembly. Some attachment mechanisms have holes or apertures about which straps or a headgear system can attach themselves thereto.

These aspects of the invention are not meant to be exclusive and other features, aspects, and advantages of the present invention will be readily apparent to those of ordinary skill in the art when read in conjunction with the following description, appended claims, and accompanying drawings. Further, it will be appreciated that any of the various features, structures, steps, or other aspects discussed herein are for purposes of illustration only, any of which can be applied in any combination with any such features as discussed in alternative embodiments, as appropriate.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

To provide an overall understanding of the systems, devices, and methods described herein, certain illustrative embodiments will be described. Although the embodiments and features described herein are frequently described for use in connection with CPAP apparatuses, systems, and methods, it will be understood that all the components, mechanisms, systems, methods, and other features outlined below can be combined with one another in any suitable manner and may be adapted and applied to other PAP apparatuses, systems, and methods, including, but not limited to, APAP, VPAP, and BPAP apparatuses, systems, and methods.

The present invention seeks to provide a lightweight and comfortable nasal mask for use with positive airway pressure supply systems by creating an adjustable, comfortable, nasal mask assembly system that has interchangeable components, is lightweight, and provides a uniform sealing around the user's nose and nasal area that is enabled by a unique internal support structure.

Figure 1:
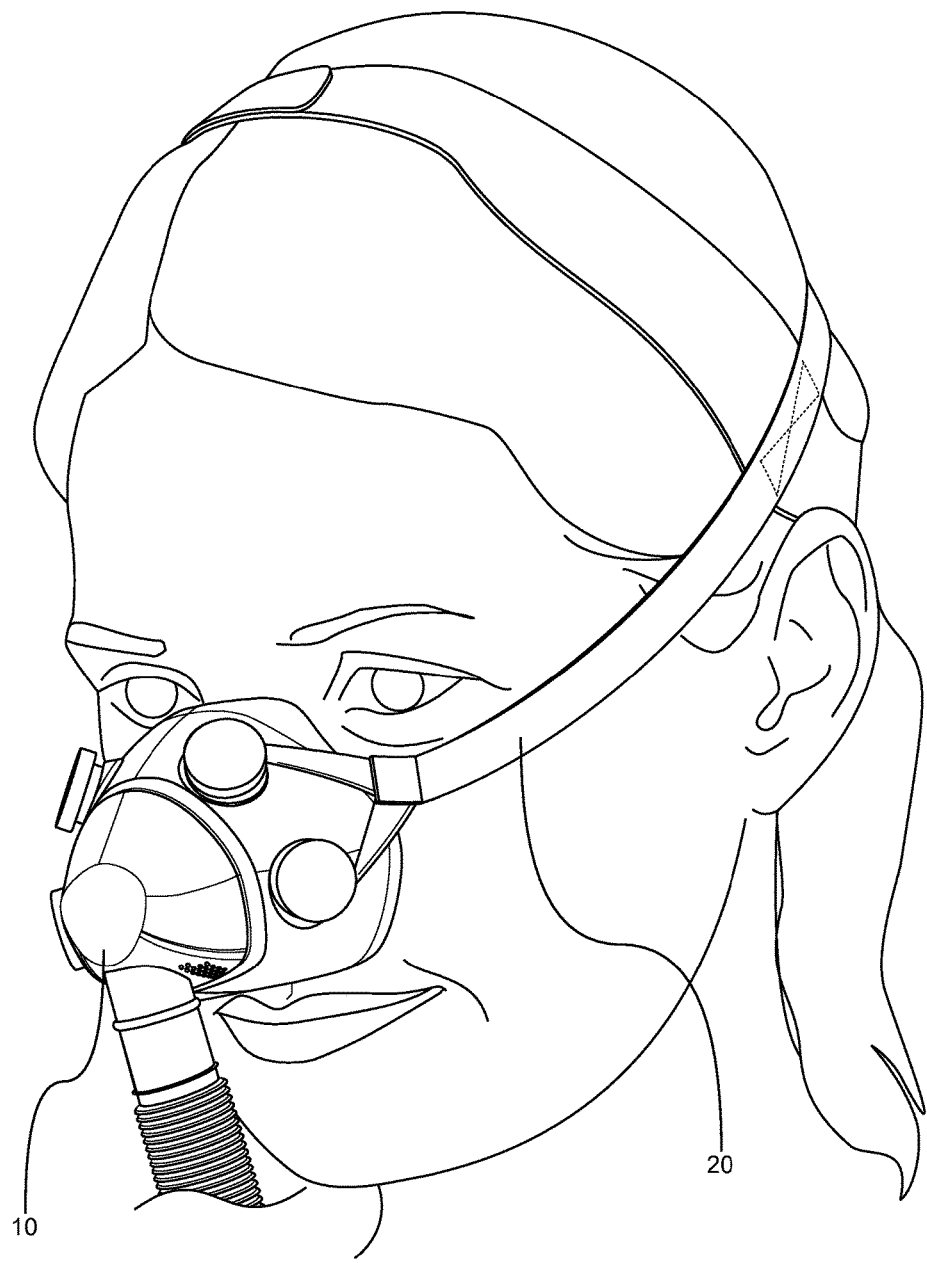
FIG. 1 illustrates a perspective view of a user wearing a nasal mask for use with positive airway pressure systems in accordance with one aspect of the present invention.
Figure 2A:
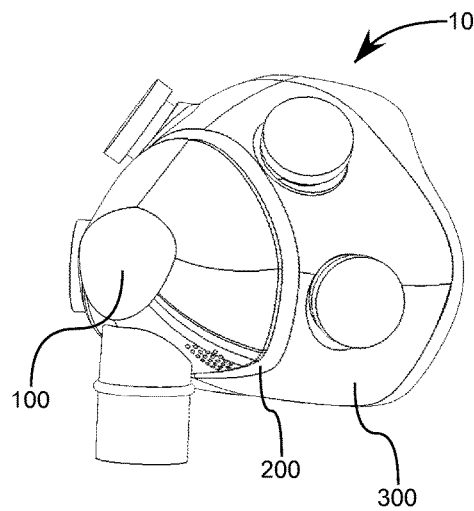
FIGS. 2A-D illustrate side perspective, front, side, and bottom views respectively of the nasal mask for use with positive airway pressure systems in accordance with the embodiment shown in FIG. 1.
Figure 2B:
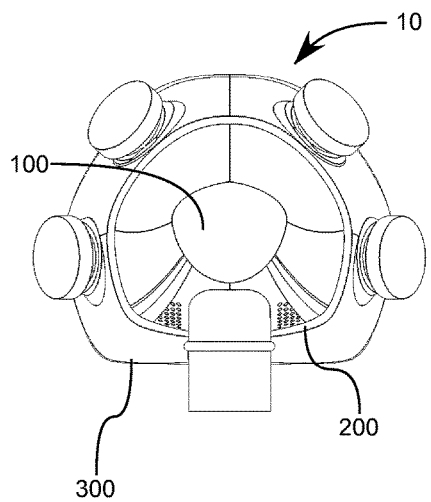
Figure 2C:
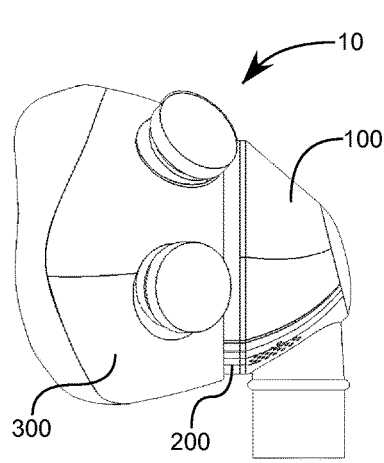
Figure 2D:
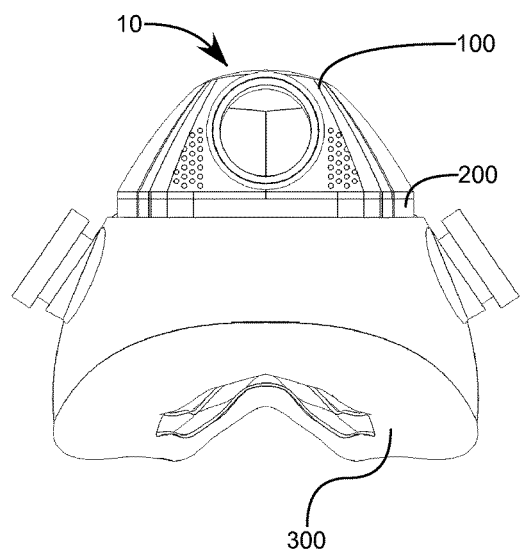
Figure 3:
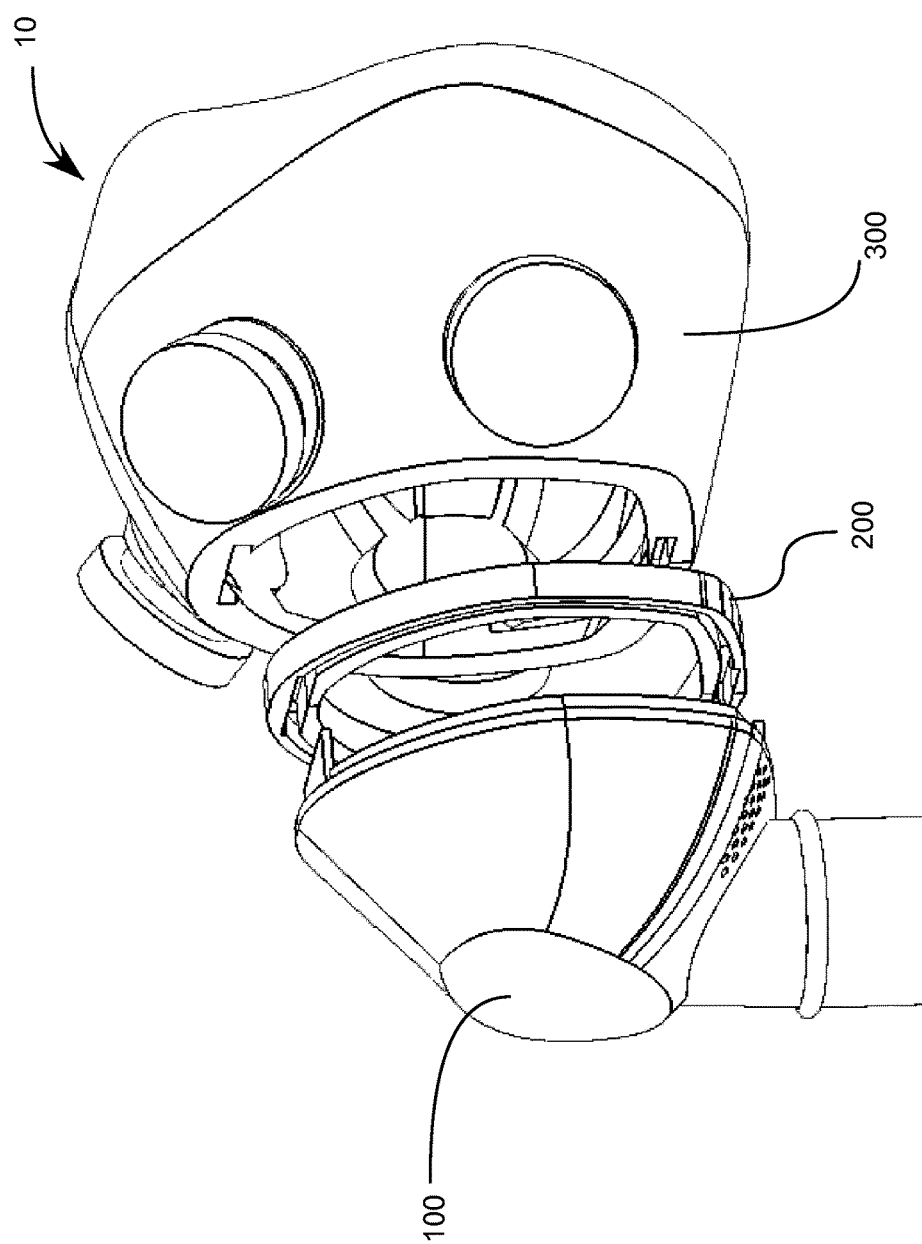
FIG. 3 illustrates an exploded view of the nasal mask for use with the positive airway pressure systems in accordance with the embodiment shown in FIG. 1.

FIG. 1 illustrates a nasal mask system 10 including a headgear or strap assembly 20 configured to attach the nasal mask system 10 to the face of a user. In particular the headgear or strap assembly 20 is configured to provide a tensile force which is transmitted into a user interface of the nasal mask system and thus translate the tensile force into a position retention force upon the user's face and deform components of the nasal mask system around the user's nose so as to create a seal around the user's nasal passages. In this manner pressurized air supplied to an interior cavity of the nasal mask system 10 will be transmitted into the nasal passages of the user in a pressurized state.

FIGS. 2A-D and 3 illustrate various assembled and exploded views of the nasal mask system 10 which is formed essentially of 3 components: an input adapter 100 configured to attach to a positive air pressure source and provide the pressurized air into a user interface or mask 300. The mask 300 is formed of a relatively flexible and thin outer shell 314 (labelled in FIG. 6) provided over, overmolded onto, or coupled to a relatively more rigid interior support structure 310 (shown in FIGS. 5A-B).

The internal support structure 310 operates to suspend and provide support to the relatively flexible and thin outer shell 314 which would otherwise have insufficient structural support. This combination allows for a thinner outer shell 314 to be suspended between the interconnected truss or web structure of the internal support and thus allows for a thinner exterior wall and ultimately a lighter and thus more comfortable mask. It will then be further appreciated that because the mask 300 can thus be difficult to couple with, being relatively flexible, or in other words will be easy to pull away from the otherwise relatively rigid input adapter 100, a rigid coupler 200 can be provided between the input adapter 100 and the mask 300 to facilitate a more secure connection between the two.

Figures 4A, 4B:
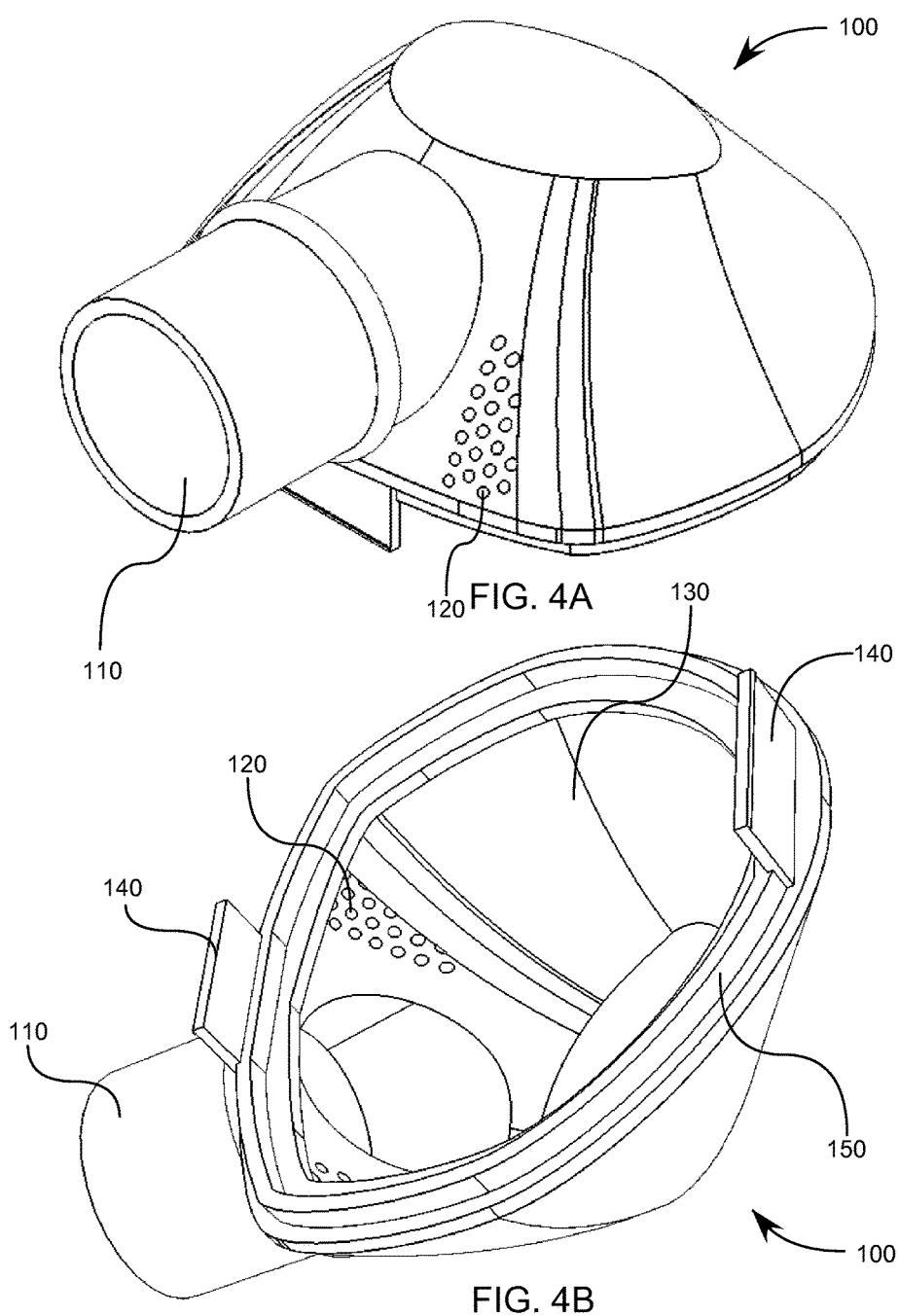
FIGS. 4A-B illustrate front and rear perspective views of an input adapter for use with the nasal mask and positive airway pressure systems in accordance with the embodiment shown in FIG. 1.

FIGS. 4A-B illustrate front and rear perspective views of an exemplary input adapter 100 being configured to couple to the inlet aperture of the mask 300, the input adapter having either a higher durometer or thicker sidewalls than the mask. The inlet adapter 100 can include a hose adapter 110 which can be configured to attach to a positive pressure air supply (not shown) so as to facilitate the provision of a pressurized air flow into the internal cavity of the mask. The inlet adapter 100 can also include a plurality of $CO_2$ washout vents 120 which can be configured in various orientations and number so as to achieve a suitable dissipation of $CO_2$ exhaled by the user into the mask assembly. It will be appreciated that these $CO_2$ washout vents 120 are shown herein the bottom portion of the adapter, but can also be provided in the front or top surfaces as well. Alternatively, these washout vents can also be provided through the mask assembly so as to achieve a proper amount of $CO_2$ venting. The inlet adapter comprises an outlet aperture 130 that is in fluid communication with the inlet aperture 360 of the mask 300.

The inlet adapter can also be provided with one or more attachment clips 140 for facilitating the coupling of the inlet adapter to either the nasal mask 300, the rigid coupler 200, or both. It will be appreciated that while these attachment clips 140 are shown as a male component of an interference latch system, any number of attachment means and orientations will be recognized by those having skill in the art as being suitable for providing a compressive sealing force between the inlet adapter and an inlet aperture of the mask.

Figure 7:
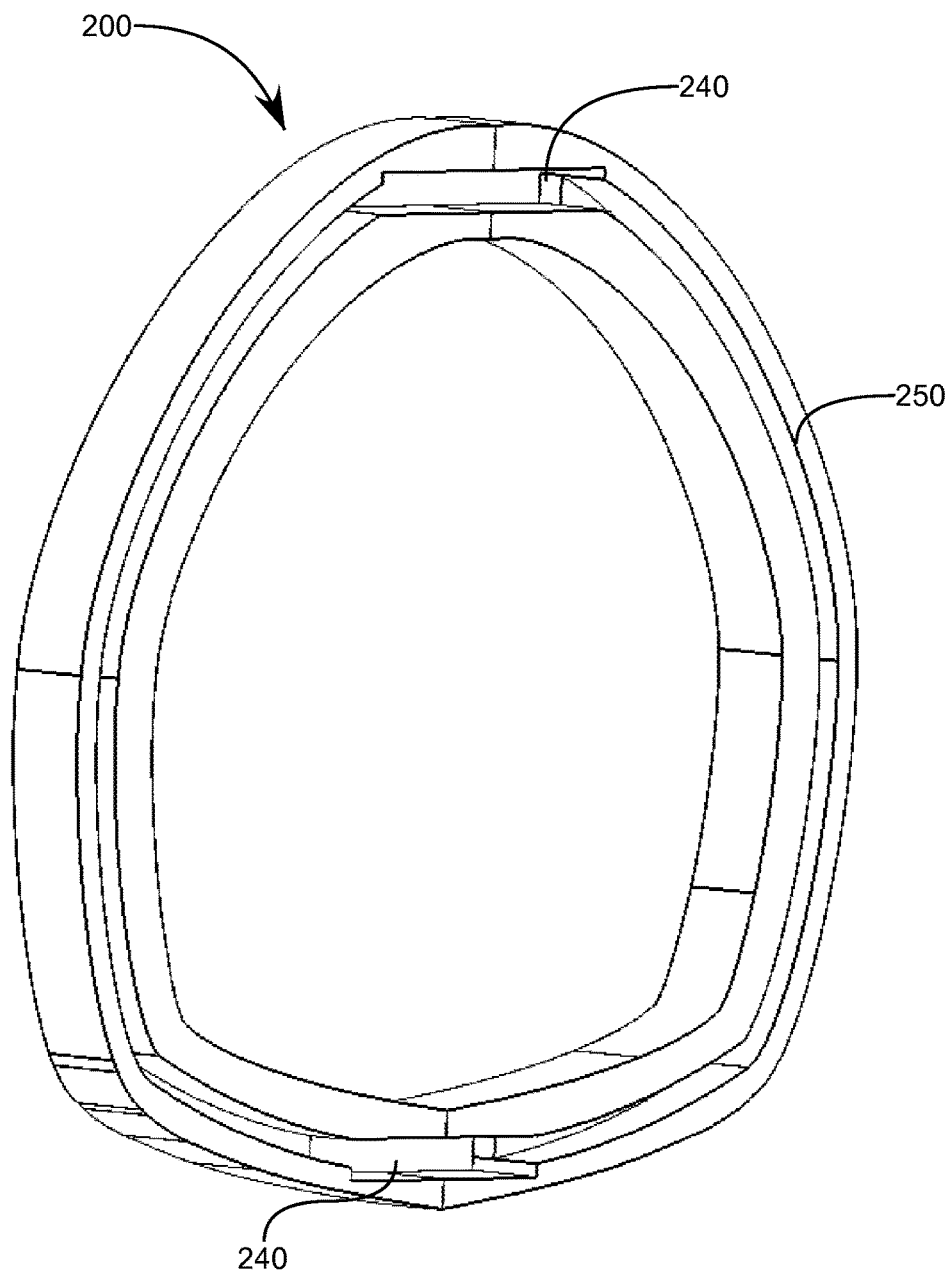
FIG. 7 illustrates perspective view of a coupling interface for coupling the input adapter as illustrated in FIGS. 4A-B to the user interface as illustrated in FIGS. 5-6.

Additionally, in the embodiment shown, the inlet adapter 100 can be provided with a sealing lip 150 which will interface with a sealing channel 250 of the coupler 200, as seen in FIG. 7. This sealing channel 250 and sealing lip 150 correspond in shape so as to provide an air tight seal between the inlet adapter 100 and the coupler 200.

Figure 5A:
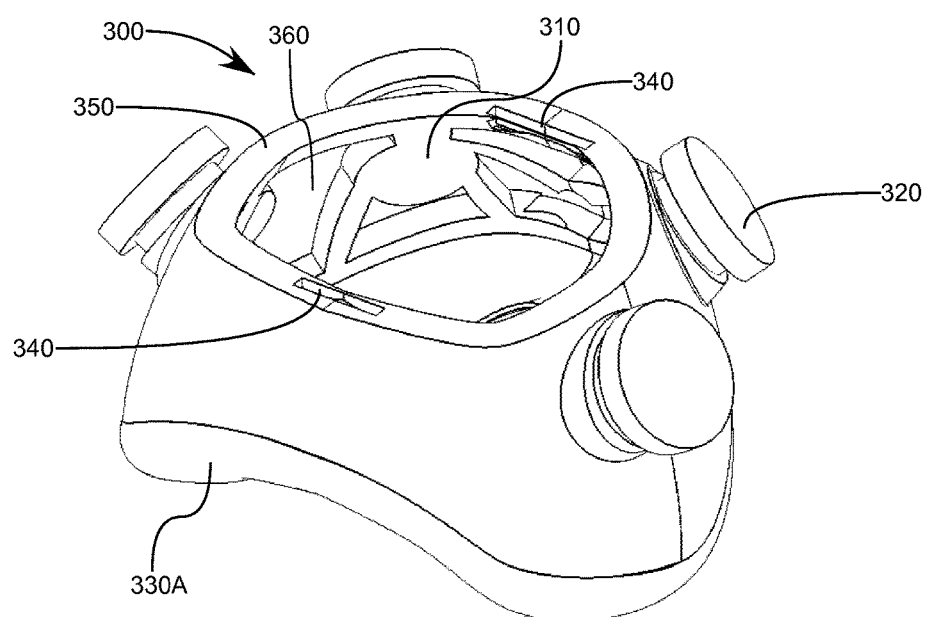
FIGS. 5A-B illustrate front and rear perspective views of a user interface for use with the nasal mask and positive airway pressure systems in accordance with the embodiment shown in FIG. 1.
Figure 5B:
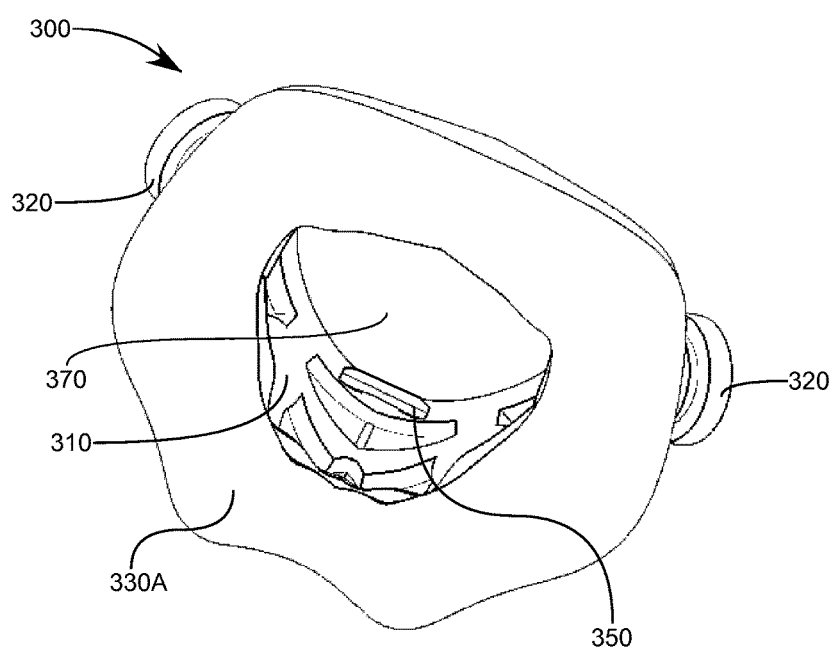
Figure 6:
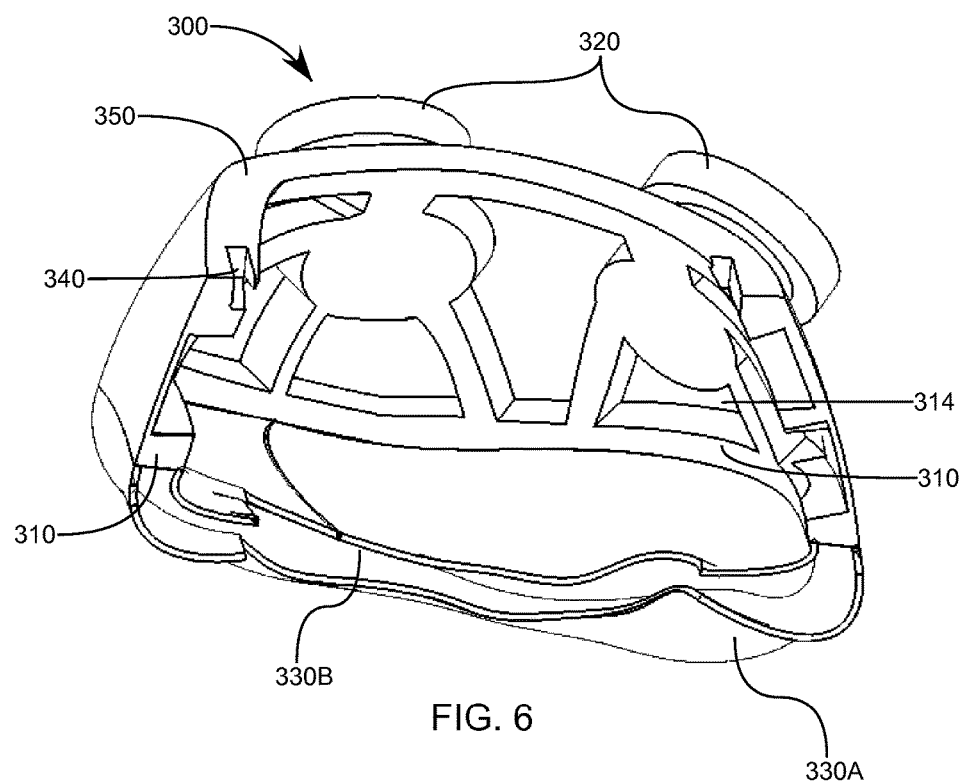
FIG. 6 illustrates a side cross sectional view of a user interface for use with the nasal mask and positive airway pressure systems in accordance with the embodiment shown in FIG. 1.

FIGS. 5A-B and FIG. 6 illustrate various views of a nasal mask 300 in accordance with various aspects of the present invention. The nasal mask 300 can include an internal support structure 310, and an external shell 314 disposed over the internal support structure 310. The external shell 314 can be formed unitarily with the internal support structure 310 using common materials or the external shell 314 can be overmolded over the internal support structure 310 using differing materials.

The internal support structure 310 is configured such that the mask remains semi-flexible but is still retains sufficient structural support so as to provide a uniform sealing force on the user's face as provided by the headgear or strap assembly 20.

The nasal mask 300 can be further provided with a plurality of attachment mechanisms 320. It will be appreciated that the attachment mechanisms 320 as shown are provided as a plurality of circular posts having mushroomed or larger top portions for engaging with corresponding loops provided on the headgear strap assembly 20. These posts allow a degree of freedom in rotational motion at the attachment point between the headgear assembly and these attachment mechanisms. It is further appreciated that the attachment mechanisms are tied into the internal support structure 310 through the external shell 314 so as to better transfer the sealing force from the headgear assembly 20 through the internal support structure and evenly onto the user's face around the user's nose. It will be further appreciated that other attachment mechanisms, as will be appreciated by those having skill in the art, can be substituted into the nasal mask shown without departing from the scope of the present invention. These could include attachment mechanisms with slots or holes, those with rib features, those with male or female connection points, and so forth.

The nasal mask 300 can be further provided with an attachment surface 350 and clip interfaces 340 about its inlet aperture 360 so as to facilitate coupling of the nasal mask 300 to the coupler 200 or directly to the inlet adapter 100.

In this manner the nasal mask 300 can be provided with a consistent bonding surface for bonding to the coupler 200 using adhesives or other suitable bonding agents. Alternatively, the nasal mask 300 can be overmolded over the coupler 200 so as to integrate the coupler 200 into the inlet aperture 360.

Additionally, the nasal mask 300 can be provided with one or more sealing membranes 330A-B which can be provided about the user interface aperture 370, wherein the sealing membranes are configured to be the contact surface between the mask 300 and the user's face. These sealing membrane can be oriented so as to extend inwardly into an internal cavity of the mask wherein the first sealing membrane 330A extends from an external edge of the internal support structure and The second malleable sealing membrane 330B extends from an internal edge of the internal support structure and thus a gap is formed therebetween so as to provide a better cushion between the user's face and the internal support structure.

In some embodiments the malleable sealing membranes can be formed unitarily of a common material with the external shell, or alternatively the malleable sealing membranes can be formed separately from the nasal mask of differing materials.

FIG. 7 illustrates a rigid coupler 200. As discussed briefly above, the rigid coupler 200 is intended to serve as a more secure attachment means between the inlet adapter 100 and the semi-flexible mask 300. As such the rigid coupler 200 can be permanently, unitarily formed with, or otherwise provided with a secure connection to the semi-flexible mask 300. The rigid coupler 200 can be provided with a sealing channel 250 for interfacing with, and providing an air tight seal to, the inlet adapter 100. Alternatively, the sealing channel 250 can also be provided on the inlet adapter 100 wherein the sealing protrusion 150 can then be provided on the coupler 200.

The rigid coupler 200 can further be provided with clip slots 240 for interfacing with the clips 140 of the inlet adapter, or alternatively the clip slots 240 can merely be pass through slots allowing the clip protrusions 140 to interface directly with the corresponding clip interfaces 340 of the mask 300 itself. As discussed above, if the rigid coupler is formed unitarily or overmolded by the mask 300 it will then be unnecessary for both the mask and the rigid coupler to have corresponding clip interfaces.

Figure 8A:
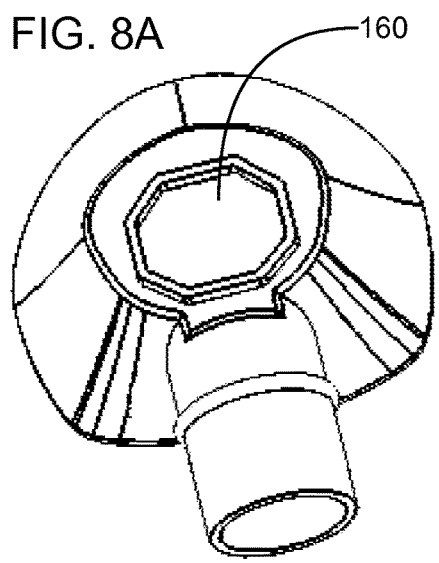
FIGS. 8A-B illustrate an alternative input adapter for use with the nasal mask and positive airway pressure systems in accordance with the embodiment shown in FIG. 1 as well as a carbon dioxide washout vent insert for use therewith.
Figure 8B:
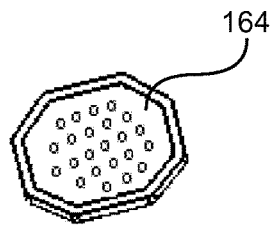

In some alternative embodiments, and as shown in FIGS. 8A-B, an alternative input adapter 100B can be used which has a venting aperture 160 provided therein. The venting aperture 160 can be provided with a removable insert 164 which can have varying components provided therethrough. As illustrated, the removable insert 164 includes a plurality of $CO_2$ washout vents provided therein which $CO_2$ to vent therethrough and out of the mask assembly 10. In such embodiments the desired amount of $CO_2$ venting can be altered by providing more or fewer micro apertures in varying inserts. In this manner the $CO_2$ venting can be altered merely by changing inserts.

Figure 9:
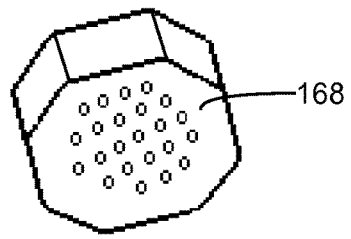
FIG. 9 illustrates perspective view of a heat moisture exchange insert for placement within any of the various embodiments of the nasal mask or components shown above.

FIG. 9 illustrates an exemplary heat moisture exchange (HME) in the form of a porous member 168. The HME 168 can be formed of varying materials, porous, wicking, or otherwise so as to retain exhaled moisture within the mask which can then be partially evaporated or entrained into the inlet air supply and thus increase the moisture content of the air supply and reduce the harshness of the supplied air. This HME 168 can be formed in varying shapes and thicknesses so as to be adaptable for use in either of the input adapters disclosed herein, or alternatively, within the nasal mask cavity.

Also contemplated herein is a method of providing a semi-flexible airway interface system, the method can include various steps, including but not limited to: providing an internal support structure; overmolding an external shell over the internal support structure, the overmolding process leaving both an interface aperture and an inlet aperture so as to form a nasal mask; providing a plurality of attachment mechanisms which extend through the external shell so as to mechanically couple to the internal support structure; providing an input adapter and affixing the inlet aperture to the inlet aperture, wherein the input adapter has a higher durometer (or thickness) than the nasal mask; applying a force to the attachment mechanisms, such that the force is transmitted through the nasal mask and causes the nasal mask to sealingly engage around a user's nose.

The method can further include the steps of providing a removable heat moisture exchange disposed within the input adapter; providing one or more $CO_2$ washout vents being provided through the input adapter.

The method can further include providing $CO_2$ washout vents through a removable insert which covers a front aperture of the input adapter.

In yet additional embodiments the method can include providing a rigid coupler provided about the inlet aperture of the nasal mask wherein the rigid coupler can be overmolded into the external shell of the nasal mask.

In yet additional embodiments the method can include providing one or more malleable sealing membranes disposed about the user interface aperture of the nasal mask by providing a first malleable sealing membrane about the interface aperture, the first malleable sealing membrane extending inwardly into an internal cavity of the mask from an external edge of the internal support structure and by providing a second malleable sealing membrane about the interface aperture, the second malleable sealing membrane extending inwardly into the internal cavity of the mask from an internal edge of the internal support structure.

It will be appreciated that individual users may have different sized noses and faces, thus the nasal mask 300 as shown herein can be scaled to fit various users wherein the rigid coupler 200 remains constant in size so as to facilitate a universal fit with a common input adapter 100.

The above embodiments can be formed of various materials including silicone materials, plastics, and the like. Furthermore, the durometer of each of the materials may be varied. For example, the durometer of the outer shell may be more pliable compared to the internal support structure. Alternatively, the thicknesses of the internal support structure may vary to provide the necessary mechanical coupling of a force being applied to the attachment means. Durometer refers to a materials hardness or rigidity.

The above embodiments described have included the guiding principles for creating and using a lightweight, flexible nasal mask system that conforms to the area around a user's nose or nasal region. Stated more explicitly these principles or features include providing 1) an internal support structure where 2) a lightweight shell can be formed over, 3) providing attachment mechanisms that mechanically couple to the internal support structure, whereby a 4) force applied to the attachment mechanisms is transferred through the internal support structure, and 5) providing a malleable interface that conforms around the nasal region, when the force transfers through the internal support structure to form a sealing region. The nasal mask can be formed of a unitary structure and have portions with varying durometer or thicknesses or it can be formed of multiple components as described above.

The double membranes are meant to assist with forming the seal, but a single membrane could also be used. A y-shaped strap 20 is shown in FIG. 1, but two single straps or even a single strap without a y-shape end are contemplated, which means two, or four or more attachment mechanisms could be provided. A removable and variable $CO_2$ vent, where the vent can be replaced according to a user's comfort level. For example, some $CO_2$ vents can provide more venting (less internal pressure) while others provide less (with the internal pressure in the mask, when exhaling being higher).

The above description is merely illustrative. Having thus described several aspects of at least one embodiment of this invention including the preferred embodiments, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only. Additionally, any features or advantages discussed in relation to any one embodiment will be understood as being applicable to any other embodiment without departing from the scope of the proposed invention as contemplated herein.

What is claimed is:

1. A positive airway interface system comprising:
a nasal mask comprising:
an internal support structure comprising an interconnected truss or web structure; wherein the internal support structure comprises a plurality of attachment mechanisms extending from the interconnected truss or web structure; wherein the plurality of attachment mechanisms are formed of a plurality of circular grommets being configured to affix to corresponding loops of a headgear assembly;
a flexible and thin external shell disposed over the internal support structure; the external shell having insufficient structural support to support itself and is supported by the internal support structure;
a user interface aperture; and
an inlet aperture;
wherein the plurality of attachment mechanisms extends through the external shell from the internal support structure.

2. The positive airway interface system of claim 1, comprising an input adapter being configured to couple to the inlet aperture of the mask, the input adapter having a higher durometer than the nasal mask.

3. The positive airway interface system of claim 2, comprising a removable heat moisture exchange disposed within the input adapter.

4. The positive airway interface system of claim 2, comprising a rigid coupler provided about the inlet aperture of the nasal mask.

5. The positive airway interface system of claim 4, wherein the rigid coupler is overmolded by the external shell of the nasal mask.

6. The positive airway interface system of claim 1, comprising one or more CO2 washout vents.

7. The positive airway interface system of claim 6, wherein the CO2 washout vent(s) are provided in a removable insert which covers a front aperture of the input adapter.

8. The positive airway interface system of claim 1, comprising one or more malleable sealing membranes disposed about the user interface aperture of the nasal mask.

9. The positive airway interface system of claim 8,
wherein the one or more malleable sealing membranes comprise:
A first malleable sealing membrane extending inwardly into an internal cavity of the mask from an external edge of the internal support structure; and
a second malleable sealing membrane extending inwardly into the internal cavity of the mask from an internal edge of the internal support structure.

10. A method of using a semi-flexible airway interface system, the method comprising:
placing a nasal mask system over a user's nasal region, wherein the nasal mask system comprises:
an internal support structure comprising an interconnected truss or web structure; wherein the internal support structure comprises a plurality of attachment mechanisms extending from the interconnected truss or web structure; wherein the plurality of attachment mechanisms are formed of a plurality of circular grommets being configured to affix to corresponding loops of a headgear assembly;
a flexible and thin shell formed over the internal support structure, the external shell having insufficient structural support to support itself and is supported by the internal support structure;
an interface aperture formed about the internal structure,
an inlet aperture formed about the internal structure,
affixing the nasal mask system about a user's nasal region using a strap of the headgear assembly that connects to the attachment mechanisms and extends around a user's head,
wherein the plurality of attachment mechanisms extends through the shell from the internal support structure.

11. The method of claim 10, wherein the nasal mask system comprises an input adapter in fluid communication to sealingly engage a user's nasal region.

12. The method of claim 11, wherein the nasal mask system further comprises one or more CO2 washout vents being provided through the input adapter.

13. The method of claim 12, wherein the CO2 washout vents are removable.

14. The method of claim 11, wherein the input adapter includes a rigid coupler provided about the inlet aperture of the nasal mask.

15. The method of claim 11, wherein the nasal mask comprises a rigid coupler disposed between the input adapter and the inlet aperture.

16. The method of claim 10, wherein the nasal mask system comprises one or more malleable sealing membranes disposed about the interface aperture.

17. The method of claim 10,
wherein the one or more malleable sealing membranes comprise:
a first malleable sealing membrane about the interface aperture, the first malleable sealing membrane extending inwardly into an internal cavity of the mask from an external edge of the internal support structure; and
a second malleable sealing membrane about the interface aperture, the second malleable sealing membrane extending inwardly into the internal cavity of the mask from an internal edge of the internal support structure.

18. A nasal mask system comprising:
an internal support structure comprising an interconnected truss or web structure; wherein the internal support structure comprises a plurality of attachment mechanisms extending from the interconnected truss or web structure; wherein the plurality of attachment mechanisms are formed of a plurality of circular grommets being configured to affix to corresponding loops of a headgear assembly;
a flexible and thin external shell disposed over the internal support structure, the external shell having insufficient structural support to support itself and is supported by the internal support structure;
wherein the plurality of attachment mechanisms extends from the internal support structure through the external shell;
a user interface aperture;
an inlet aperture;
a first malleable sealing membrane extending inwardly into an internal cavity of the mask from an external edge of the internal support structure; and
a second malleable sealing membrane extending inwardly into the internal cavity of the mask from an internal edge of the internal support structure.

* * * * *